United States Patent
Siemionow (10) Patent No.: US 11,147,840 B2
(45) Date of Patent: Oct. 19, 2021

(54) MUSCULAR DYSTROPHY CHIMERIC CELLS AND METHOD FOR TREATING MUSCULAR DYSTROPHIES

(71) Applicant: The Board of Trustees of the University of Illinois, Chicago, IL (US)

(72) Inventor: Maria Siemionow, Chicago, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 223 days.

(21) Appl. No.: 15/580,783

(22) PCT Filed: Jun. 10, 2016

(86) PCT No.: PCT/US2016/036821
§ 371 (c)(1),
(2) Date: Dec. 8, 2017

(87) PCT Pub. No.: WO2016/201182
PCT Pub. Date: Dec. 15, 2016

(65) Prior Publication Data
US 2018/0221416 A1    Aug. 9, 2018

Related U.S. Application Data

(60) Provisional application No. 62/174,122, filed on Jun. 11, 2015.

(51) Int. Cl.
| A61K 35/34 | (2015.01) |
| C12N 5/077 | (2010.01) |
| C12N 5/0775 | (2010.01) |
| C12N 5/16 | (2006.01) |
| A61P 25/14 | (2006.01) |
| A61P 21/00 | (2006.01) |
| A61K 9/00 | (2006.01) |
| A61K 45/06 | (2006.01) |

(52) U.S. Cl.
CPC ............ *A61K 35/34* (2013.01); *A61K 9/0019* (2013.01); *A61K 45/06* (2013.01); *A61P 21/00* (2018.01); *A61P 25/14* (2018.01); *C12N 5/0658* (2013.01); *C12N 5/0663* (2013.01); *C12N 5/16* (2013.01); *C12N 2510/00* (2013.01)

(58) Field of Classification Search
CPC ...... A61K 35/34; A61K 45/06; A61K 9/0019; A61P 21/00; A61P 25/14; C12N 2510/00; C12N 5/0658; C12N 5/0663; C12N 5/16
USPC ...................... 424/93.21; 435/325
See application file for complete search history.

(56) References Cited

U.S. PATENT DOCUMENTS

| 7,341,719 | B1 | 3/2008 | Law | 424/93.7 |
| 7,452,529 | B2 | 11/2008 | Brown, Jr. et al. | 424/93.1 |
| 7,887,793 | B2 | 2/2011 | Tremblay et al. | 424/93.21 |
| 2002/0127690 | A1* | 9/2002 | Olson | C07K 14/47 435/226 |
| 2006/0251632 | A1 | 11/2006 | Tremblay et al. | 424/93.21 |
| 2007/0253931 | A1* | 11/2007 | Varney | C12N 5/0663 424/93.1 |
| 2008/0299091 | A1* | 12/2008 | Revazova | C12N 5/0606 424/93.7 |
| 2011/0250691 | A1* | 10/2011 | Parent | A61P 21/00 435/406 |
| 2014/0199377 | A1* | 7/2014 | Stankus | A61K 9/127 424/450 |

FOREIGN PATENT DOCUMENTS

| JP | H10505756 | 9/1998 |
| JP | 2011514901 | 5/2011 |
| WO | WO 96/09373 A1 | 3/1996 |
| WO | WO96/18303 | 6/1996 |
| WO | WO-9618303 A1 * | 6/1996 ............. A61K 35/34 |
| WO | WO 2009/111030 A1 | 9/2009 |
| WO | WO2014/210448 | 12/2014 |
| WO | WO-2014210448 A1 * | 12/2014 |

OTHER PUBLICATIONS

Shi et al. Blood, vol. 104, No. 1, pp. 290-296. (Year: 2004).*
Konieczny et al. The Journal of Cell Biology . vol. 97 Nov. 1983 1348-1355 (Year: 1983).*
Goudenage et al. "Myoblasts derived from normal hESCs and dystrophic hiPSCs efficiently fuse with existing muscle fibers following transplantation" Molecular Therapy 2012 20(11):2153-2167.
Meregalli et al. "Stem cell therapies to treat muscular dystrophy" Biodrugs 2010 24(4):237-247.
Partridge et al. "Evidence of fusion between host and donor myoblasts in skeletal muscle grafts" Nature 1978 273 (25) :306-308.
Shi et al. "Myogenic fusion of human bone marrow stromal cells, but not hematopoietic cells" Blood 2004 104(1):290-294.
International Search Report and Written Opinion in PCT/US2016/036821 dated Sep. 7, 2016.
International Preliminary Report on Patentability in PCT/US2016/036821 dated Dec. 21, 2017.
Extended European Search Report in Application No. 16808341.8 dated Mar. 27, 2018.
Eom et al. "Effective Myotube Formation in Human Adipose Tissue-Derived Stem Cells Expressing Dystrophin and Myosin Heavy Chain by Cellular Fusion with Mouse C2C12 Myoblasts" Biochemical and Biophysical Research Communications (2011) 408:167-173.

* cited by examiner
(Continued)

*Primary Examiner* — Janet L Epps-Smith
(74) *Attorney, Agent, or Firm* — Licata & Tyrrell P.C.

(57) ABSTRACT

A Muscular Dystrophy Chimeric Cell generated by ex vivo fusion of a myoblast with a second myoblast, mesenchymal stem cell, or stromal cell is described as is the use of the same in the treatment of a muscular dystrophy.

12 Claims, 3 Drawing Sheets

MUSCULAR DYSTROPHY CHIMERIC CELLS AND METHOD FOR TREATING MUSCULAR DYSTROPHIES

INTRODUCTION

This application is a U.S. National Stage Application of PCT/US2016/036821 filed Jun. 10, 2016 and claims benefit of priority to U.S. Provisional Patent Application Ser. No. 62/174,122, filed Jun. 11, 2015, the contents of each of which are incorporated herein by reference in their entirety.

BACKGROUND

Muscular dystrophies (MD) are a group of more than 30 genetic diseases characterized by progressive weakness and degeneration of the skeletal muscles that control movement. Some forms of MD are seen in infancy or childhood, while others may not appear until middle age or later. The disorders differ in terms of the distribution and extent of muscle weakness (some forms of MD also affect cardiac muscle), age of onset, rate of progression, and pattern of inheritance.

Duchenne muscular dystrophy (DMD), the most common, lethal X-chromosome linked progressive muscle-wasting disorder, is caused by dystrophin gene mutations resulting in the absence of dystrophin, a protein involved in maintaining the integrity of muscle. DMD affects 1 in every 3500 male births. Onset is between 3 and 5 years and the disorder progresses rapidly. Most boys are unable to walk by age 12, and later need a respirator to breathe. Girls in these families have a 50 percent chance of inheriting and passing the defective gene to their children. Debilitated patients cannot partake in routine activities; most are wheelchair-dependent by the age of 12. Life expectancy of DMD patients is 25. Boys with Becker MD (very similar to but less severe than Duchenne MD) have faulty or not enough dystrophin.

Facioscapulohumeral MD usually begins in the teenage years. It causes progressive weakness in muscles of the face, arms, legs, and around the shoulders and chest. It progresses slowly and can vary in symptoms from mild to disabling.

Myotonic MD is the disorder's most common adult form and is typified by prolonged muscle spasms, cataracts, cardiac abnormalities, and endocrine disturbances. Individuals with myotonic MD have long, thin faces, drooping eyelids, and a swan-like neck.

Muscular dystrophies are caused by progressive degeneration of skeletal muscle fibers. Lack of one of several proteins located either at the plasma membrane or, less frequently, within internal membranes increases the probability of damage during contraction, and eventually leads to fiber degeneration, accompanied by severe local inflammation with infiltration of immune-competent cells. In the most severe forms, such as Duchenne Muscular Dystrophy, regeneration is exhausted and skeletal muscle is progressively replaced by fat and fibrous tissue. This condition leads the patient to progressive weakness and eventually death by respiratory and/or cardiac failure.

At present, an effective therapy for MD has not been found yet, and importance is placed on rehabilitation for retarding the progression of symptoms or respiratory management using mechanical ventilators or the like. Drug therapy includes corticosteroids (steroids), but they have strong side effects and have not produced sufficient therapeutic effect. Experimental therapies such as regenerative therapy (transplantation of stem cells and myoblasts) (Meregalli, et al. (2010) *BioDrugs* 24:237-247; U.S. Pat. Nos. 7,341,719; 7,887,793; and 7,452,529), gene therapy (functional dystrophin gene transfer, antisense morpholino-mediated skipping of mutated exons), alternative drug therapy (read-through of nonsense mutations) and the like have been suggested. However, there is an urgent need to develop new, more effective strategies to treat patients with MD.

SUMMARY OF THE INVENTION

This invention provides a Muscular Dystrophy Chimeric Cell (MDCC) prepared by fusion of (a) a first myoblast; and (b) a second myoblast, mesenchymal stem cell, or stromal cell, wherein at least one of the first myoblast, second myoblast, mesenchymal stem cell, or stromal cell is from a healthy donor. In some embodiments, the first myoblast and second myoblast are from different donors. In other embodiments, the first myoblast, second myoblast, mesenchymal stem cell, or stromal cell is autologous or allogeneic. In particular embodiments, the healthy donor is the subject's father. In further embodiments, the mesenchymal stem cells are derived from bone marrow or adipose tissue and the MDCC secretes one or more immunomodulatory cytokines and growth factors, e.g., insulin-like growth factor 1, hepatocyte growth factor and myostatin. A composition containing the MDCC, a kit, and a method of administering the MDCC by intravenous injection, intra-bone injection or intramuscular injection in the treatment of a muscular dystrophy such as Duchenne Muscular Dystrophy are also provided.

BRIEF DESCRIPTION OF THE DRAWINGS

FIG. 1 shows the ex vivo fusion procedure to create human MDCC. In one embodiment, human myoblasts are obtained from a DMD patient's muscle and are fused with myoblasts or mesenchymal stem cells (MSC) from a healthy donor. Prior to fusion, cells are fluorescently labeled with PKH26 or PKH67, respectively. Cell fusion of fluorescently labeled cells is performed using polyethylene glycol (PEG). Double (PKH26 and PKH67) stained cells that undergo fusion are selected via fluorescently activated cells sorting (FACS; BD Asterios). These cells are delivered through intramuscular injection into DMD patient deteriorating muscles.

FIGS. 3A and 3B show the results of an in vivo muscular contractility test. Muscle force (FIG. 3A) and percent fatigue (FIG. 3B) measurements were normalized with the muscle weights. hMDCC-treated animals showed improved muscle force (p=0.04) and fatigue tolerance 90 days after MDCC local injections.

FIGS. 4A and 4B show the results of an ex vivo muscular contractility test. mMDCC-treated gastrocnemius muscles showed increased contractile strength expressed after the maximal sine wave (p=0.039; FIG. 4A) and maximal percent strain (FIG. 4B), compared to control, untreated muscle.

FIGS. 5A and 5B show the results of in vivo muscular contractility test. Muscle force (FIG. 5A) and Percent fatigue (FIG. 5B) measurements were normalized with the muscle weights. mMDCC-treated animals showed improved muscle force and fatigue tolerance (p=0.05) 30 days after MDCC local injections.

DETAILED DESCRIPTION OF THE INVENTION

MDCC compositions and methods for treating muscular dystrophies in patients have now been developed. MDCC lines are created by ex vivo fusion of a first population of myoblasts (autologous or allogeneic) with a second population of myoblasts, mesenchymal stem cells or stromal cells. Administration of the MDCC enables simultaneous delivery of myogenic and mesenchymal origin cells to patients. Accordingly, this invention provides MDCCs prepared by fusion of myoblasts from a subject suffering from a muscular dystrophy and myoblasts from a healthy donor; myoblasts from a subject suffering from a muscular dystrophy and mesenchymal stem cells; myoblasts from a healthy donor and mesenchymal stem cells; myoblasts from a subject suffering from a muscular dystrophy and stromal cells; or myoblasts from a healthy donor and stromal cells. In particular embodiments, the MDCCs of this invention find use in a method for treating muscular dystrophies.

This invention differs from other cell-based therapies since the combined therapy introduces myoblasts differentiating into myocytes, whereas MSC are known for reduced alloreactivity, plasticity and potential for de-differentiation into myoblasts in damaged tissue. Combination of myoblasts/MSC characteristics, including the secretion of immunomodulatory cytokines and growth factors, supports MDCC engraftment, tolerance and regeneration of muscle under favorable microenvironment conditions. On the other hand, myoblast/myoblast MDCC characteristics and capacity to spontaneously fuse offer the ability to either engraft and resupply the muscle stem cell niche or fuse with the recipient myoblast after treatment, providing better outcomes compared to myoblasts/MSC MDCC. Cells harvested from DMD patient may be fused with healthy, dystrophin-positive stem cells from haploidentical male relative, i.e., father or from haplo-matched donor in cell banks. In this manner, the MDCC shares surface antigens of self and haplo-identical origin, reducing the risk of rejection of transplanted MDCC. Further, given that the MDCCs are not genetically modified (i.e., by recombinant methods) and do not require immune suppression, use of the cells of this invention provides a safe alternative to conventional therapies.

For the purposes of this invention, a "chimeric cell" or "hybrid cell" is a cell that is constructed from a somatic cell hybridization (or a whole cell hybridization) of, for example, two or more biological cells (parent cells). The parent or donor cells can be obtained from either the same donor or cell lineage or different donors or cell lineage. While the MDCC of this invention is referred to as "a chimeric cell," said chimeric cell is intended to mean a single cell or a population of cells.

As used herein, a donor is a subject who provides a cell used in the preparation of a chimeric cell of this invention. The donor can be a subject with a muscular dystrophy or a healthy donor, i.e., an individual not suffering from the same genetic disorder. The donor can be the genetic father (parent) of a subject (son) with a muscular dystrophy or a cell bank donor. In particular embodiments, at least one of the donors is a healthy subject. In certain embodiments, the healthy donor is the subject's father. In other embodiments, the first myoblast, a second myoblast, mesenchymal stem cell or stromal cell is autologous or allogeneic. Further, the donor may be any mammal including a human, mouse, rat, dog, cat, horse, and the like. In particular embodiments, the donor is human.

As is convention in the art, a myoblast refers to a primitive muscle cell having the potential to develop into a muscle fiber. Myoblasts are characterized by expression of desmin and CD56, and can be obtained from fetal or adult tissue using a method known in the art. See, e.g., WO 93/03768, which discloses the isolation of myoblasts from a crude cell population by flow cytometry (e.g., FACs). Alternatively, a myoblast can be obtained by growing and propagating muscle biopsy-derived myoblasts in culture. See, e.g., Springer, et al. (1997) In: *Current Human Genetics*. Unit 13.4, Boyle Ed. John Wiley & Sons, NY. In accordance with some embodiments of this invention, a myoblast from a healthy donor is fused with a myoblast from a subject with a muscular dystrophy. In particular embodiments, a first myoblast and a myoblast are from different donors.

"Mesenchymal stem cells" (also referred to as "MSCs") can give rise to connective tissue, bone, cartilage, and cells in the circulatory and lymphatic systems. Mesenchymal stem cells are found in the mesenchyme, the part of the embryonic mesoderm that consists of loosely packed, fusiform or stellate unspecialized cells. Mesenchymal stem cells can be obtained by conventional methods and can be identified one or more of the following markers: CD29, CD31$^-$, CD34$^-$, CD44 CD45$^-$, CD51, CD73, CD90/Thy-1, CD105, CD166, Integrin α1, PDGF Rα, Nestin, Sca-1$^+$, SCF R/c-Kit, STRO-1, and VCAM-1. In some embodiments, the mesenchymal stem cells are derived or obtained from bone marrow (BM) or adipose tissue (ASC). In particular embodiments, the mesenchymal stem cells are derived or obtained from human bone marrow.

The term "stromal cell" or "adherent stromal cell" is intended to mean a cell defined by its ability to adhere and proliferate in tissue-culture treated petri dishes with or without other cells and/or elements found in loose connective tissue, including but not limited to, endothelial cells, pericytes, macrophages, monocytes, plasma cells, mast cells and adipocytes. Any suitable method can be used to obtain stromal cells. See, e.g., Tondreau, et al. (2005) *Stem Cells* 23:1105-1112. In particular embodiments, the stromal cell is derived or obtained from bone marrow (BM) or cord blood (CB). In other embodiments, the stromal cell is a CD133$^+$ stromal cell.

The cells used in the preparation of the MDCCs of this invention can be isolated and optionally purified. As used herein the term "isolated" is meant to describe a cell of interest that is in an environment different from that in which the element naturally occurs. "Purified" as used herein refers to a cell removed from an environment in which it was produced and is at least 60% free, preferably 75% free, and most preferably 90% free from other components with which it is naturally associated or with which it was otherwise associated with during production.

Purification and/or identification of cells of interest can be achieved through any means known in the art, for example immunologically. Histochemical staining, flow cytometry, fluorescence activated cell sorting (FACS), western blot analysis, enzyme-linked immunosorbent assay (ELISA), etc. may be used. Flow immunocytochemistry may be used to detect cell-surface markers, immunohistochemistry (for example, of fixed cells) may be used for intracellular or cell-surface markers. Western blot analysis may be conducted on cellular extracts. Enzyme-linked immunosorbent assay may be used for cellular extracts or products secreted into the medium. Antibodies for the identification of stem cell markers may be obtained from commercial sources, for example from Chemicon International, (Temecula, Calif.).

In some embodiments, a donor cell used in the preparation of the MDCC of this invention is autologous or heterologous to the subject being treated. In other embodiments, a donor cell used in the preparation of the MDCC of this invention is allogeneic to said subject. In certain embodiments, the donor cells are HLA (human leukocyte antigen)-matched. Representative sources of donor cells used for the preparation of the MDCCs of the invention are listed in Table 1.

TABLE 1

| Father | Son |
|---|---|
| MSC | Myoblast |
| Myoblast | Myoblast |
| Bone Marrow (BM) | Myoblast |
| MDSC | Myoblast |
| CD133+ (BM) | Myoblast |
| MSC | Muscle-derived stem cell (MDSC) |
| Myoblast | MDSC |
| Bone Marrow | MDSC |
| MDSC | MDSC |
| CD133+ (BM) | MDSC |
| Myoblast | MSC |
| Myoblast | Bone Marrow |
| ASC | Myoblast |
| ASC | ASC |

| Father | Father |
|---|---|
| MSC | Myoblast |
| CD133+ (BM) | Myoblast |
| Bone Marrow | Myoblast |
| MSC | MDSC |
| CD133+ (BM) | MDSC |
| Bone Marrow | MDSC |
| ASC | Myoblast |

| Cell Bank | Son |
|---|---|
| CD133+ (BM) | Myoblast |
| CD133+ (CB) | Myoblast |
| MSC | Myoblast |
| CD133+ (BM) | MDSC |
| CD133+ (CB) | MDSC |
| MSC | MDSC |

| Cell Bank | Father |
|---|---|
| CD133+ (BM) | Myoblast |
| CD133+ (CB) | Myoblast |
| MSC | Myoblast |
| CD133+ (BM) | MDSC |
| CD133+ (CB) | MDSC |
| MSC | MDSC |

In particular embodiments, the MDCC is produced by fusing:

a) a human myoblast from a subject suffering from a muscular dystrophy and a human myoblast from a healthy donor;

b) a human myoblast from a subject suffering from a muscular dystrophy and a human mesenchymal stem cell from a healthy donor;

c) a human myoblast from a healthy donor and a human mesenchymal stem cell from a healthy donor;

d) a human myoblast from a subject suffering from a muscular dystrophy and a human stromal cell from a healthy donor; or e) a human myoblast from a healthy donor and a human stromal cell from a healthy donor.

The MDCC of this invention is prepared by ex vivo fusion of two different donor cells. By "ex vivo" it is meant that cells are manipulated outside of the body. Cell fusion is a process in which two or more cells merge into one by fusing their plasma membranes. MDCCs can be prepared by cell fusion methods known in the art, including, but not limited to, exposure of cells to fusion-promoting chemicals, such as polyethylene glycol (PEG); the use of inactivated virus, such as Sendai virus; and the use of electrical stimulation. See, e.g., Kennett (1979) *Methods Enzymol.* 58:345-359 for a review of the commonly used methods based upon Sendai virus induced cell fusion, or cell fusion induced by polyethylene glycol (PEG). Briefly, cells to be fused are incubated with a fusogenic agent, such as Sendai virus or PEG. Centrifugation or agitation may be used to encourage clumping and close apposition of the cell membranes. Variables such as time, temperature, cell concentration and fusogenic agent concentration may be optimized for each cell combination. With respect to electro fusion, short electric pulses are passed through mixtures of cells to stimulate fusion. See, e.g., Neil & Zimmermann (1993) *Methods Enzymol.* 220: 174-196.

In certain embodiments, the MDCCs are prepared by polyethylene glycol cell fusion. After fusion, cell lines representing either myogenic/myogenic or myogenic/MSC origin are separated, cultured and characterized to confirm the myoblast and MSC specific markers and HLA class I types of cell donor origin.

Prior to fusion, the donor cells may or may not be cultured to increase their number. Further, the donor cells may or may not be labeled (e.g., with a membrane dye) to monitor fusion of the donor cells. By way of illustration, myoblasts from a subject suffering from a muscular dystrophy are labeled with PKH26-red and myoblasts from a healthy donor are labeled with PKH67-green.

In some embodiments, the MDCC of this invention secretes one or more immunomodulatory cytokines and growth factors. In certain embodiments, the immunomodulatory cytokines and growth factors include insulin-like growth factor 1 (IGF-1), hepatocyte growth factor (HGF) and myostatin. In further embodiments, the MDCC of this invention produces dystrophin.

The MDCC of this invention is of particular use in the treatment of muscular dystrophies. Accordingly, this invention also provides methods of treating muscular dystrophies in a subject in need thereof by administering to the subject the MDCC of the invention or a composition containing the MDCC in an amount effective to treat the dystrophies. "Treating" a subject having a disease or disorder means accomplishing one or more of the following: (a) reducing the severity of the disease; (b) arresting the development of the disease or disorder; (e) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (g) improving survival.

As indicated herein, muscular dystrophies are a group of genetic diseases characterized by progressive weakness and degeneration of the skeletal muscles that control movement. Examples of muscular dystrophies include Duchenne Muscular Dystrophy, Becker Muscular Dystrophy, Limb Girdle Muscular Dystrophy, Myotonic Muscular Dystrophy, Facioscapulohumeral Muscular Dystrophy, Oculopharyngeal muscular dystrophy, Emery-Dreifuss muscular dystrophy, Fukuyama-type congenital muscular dystrophy, Miyoshi myopathy, Ullrich congenital muscular dystrophy, Steinert Muscular Dystrophy. In certain embodiments, the muscular dystrophy is Duchenne muscular dystrophy (DMD).

In accordance with the method of treatment, a MDCC or composition containing the same is administered to a subject having a muscular dystrophy. In some embodiments, a combination of MDCCs of this invention can be administered. The MDCC or combination of cells can be administered by engraftment, wherein the cells are injected into the subject, for example, intravenously, intra-muscularly, intra-arterially, intra-bone and the like. In certain embodiments, administration involves engrafting about $10^2$, $10^4$, $10^6$, $10^7$, $10^8$, $10^9$, $10^{10}$, $10^{12}$, or more cells. The number of cells engrafted may be chosen based on the route of administration and/or the severity of the condition for which the cells are being engrafted. Advantageously, the MDCC of this invention will successfully engraft and complement the function of defected muscles of muscular dystrophy patients.

Compositions containing the MDCC or combinations of MDCCs can be prepared by combining the cell or combination of cells with a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and the like. The use of such media and agents for pharmaceutically active substances is well known in the art. Except insofar as any conventional media or agent is incompatible with the cells of the present disclosure, its use in therapeutic compositions is contemplated. Pharmaceutical compositions can be determined by one skilled in the art depending upon, for example, the intended route of administration, delivery format and desired dosage. See, for example, REMINGTON'S PHARMACEUTICAL SCIENCES, 18th Edition, (A. R. Gennaro, ed.), 1990, Mack Publishing Company.

The compositions of the invention can be incorporated in an injectable formulation. The formulation may also include the necessary physiologically acceptable carrier material, excipient, lubricant, buffer, surfactant, antibacterial, bulking agent (such as mannitol), antioxidants (ascorbic acid or sodium bisulfite) and the like.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials may include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA; complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS, PEG, sorbitan esters, polysorbates such as polysorbate 20 and polysorbate 80, TRITON, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, Id.

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefore. Pharmaceutical compositions of the invention may be prepared for storage by mixing the selected composition having the desired degree of purity with optional formulation agents (REMINGTON'S PHARMACEUTICAL SCIENCES, Id.) in the form of a lyophilized cake or an aqueous solution.

The cell or composition can be provided by sustained release systems, by encapsulation or by implantation devices. The compositions may be administered by bolus injection or continuously by infusion, or by implantation device. The composition also can be administered locally via implantation of a membrane, sponge or another appropriate material onto which the cell or cells have been absorbed or encapsulated. Where an implantation device is used, the device may be implanted into any suitable tissue or organ. The injections may be given as a one-time treatment, repeated (daily, weekly, monthly, annually etc.) in order to achieve the desired therapeutic effect.

Cell encapsulation methodology has been previously described which allows transplantation of encapsulated cells in treatment of Parkinson's disease (Tresco, et al. (1992) *ASAIO J.* 38:17-23) or Amyotrophic lateral sclerosis (Aebischer, et al. (1996) *Hum. Gene Ther.* 7:851-860). In accordance with this embodiment, cells are encapsulated by compounds which form a microporous membrane. Capsules, for example approximately 1 cm in length, containing the cells of interest may be prepared employing a hollow microporous membrane fabricated from poly-ether-sulfone (PES) (Akzo Nobel Faser AG, Wuppertal, Germany; Déglon, et al. (1996) *Hum. Gene Ther.* 7:2135-2146).

The compositions of the invention can be delivered parenterally. When parenteral administration is contemplated, the therapeutic compositions for use in this invention may be in the form of a pyrogen-free, parenterally acceptable aqueous solution. A particularly suitable vehicle for parenteral injection is sterile distilled water. Preparation can involve the formulation with an agent, such as injectable microspheres, bio-erodible particles, polymeric compounds (such as polylactic acid or polyglycolic acid), beads or liposomes, that may provide controlled or sustained release of the cell or cells, which may then be delivered via a depot injection.

Formulation with hyaluronic acid has the effect of promoting sustained duration in the circulation. Implantable drug delivery devices may be used to introduce the desired composition.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like.

Supplementary active ingredients also can be incorporated into the compositions. The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intraperitoneal, or intravenous injection. Intramuscular injection will be preferred. Such compositions would normally be administered as pharmaceutically acceptable compositions.

As used herein, the term "amount effective," "effective amount" or a "therapeutically effective amount" refers to an amount of the cell or composition of the invention sufficient to achieve the desired result. The amount of the cell or composition which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect.

The present invention is also directed to a kit to for the treatment of a muscular dystrophy. The kit is useful for practicing the inventive method of treating a muscular dystrophy. The kit is an assemblage of materials or components, including at least one of the inventive compositions. Thus, in some embodiments the kit a fusogenic agent for carrying out ex vivo cell fusions, and one or more donor cells (e.g., donor cells from a cell bank), and optionally materials for obtaining donor cells, as described above.

The exact nature of the components configured in the inventive kit depends on its intended purpose. For example, some embodiments are configured for the purpose of treating a muscular dystrophy. In one embodiment, the kit is configured particularly for the purpose of treating human subjects. In another embodiment, the kit is configured particularly for the purpose of treating adult, human subjects. In another embodiment, the kit is configured particularly for the purpose of treating children. In another embodiment, the kit is configured particularly for the purpose of treating DMD. In another embodiment, the kit is configured particularly for the purpose of treating BMD. In another embodiment, the kit is configured particularly for the purpose of providing continuous daily use dosages. In another embodiment, the kit is configured particularly for the purpose of providing as needed use dosages. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat muscular dystrophy, to treat BMD, or to treat DMD. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit. The packaging material is constructed by well-known methods, preferably to provide a sterile, contaminant-free environment. The packaging materials employed in the kit are those customarily utilized in therapeutic treatment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

The following non-limiting examples are provided to further illustrate the present invention.

Example 1: Ex Vivo Preparation of Human Muscular Dystrophy Chimeric Cells (hMDCC)

Figure 1:
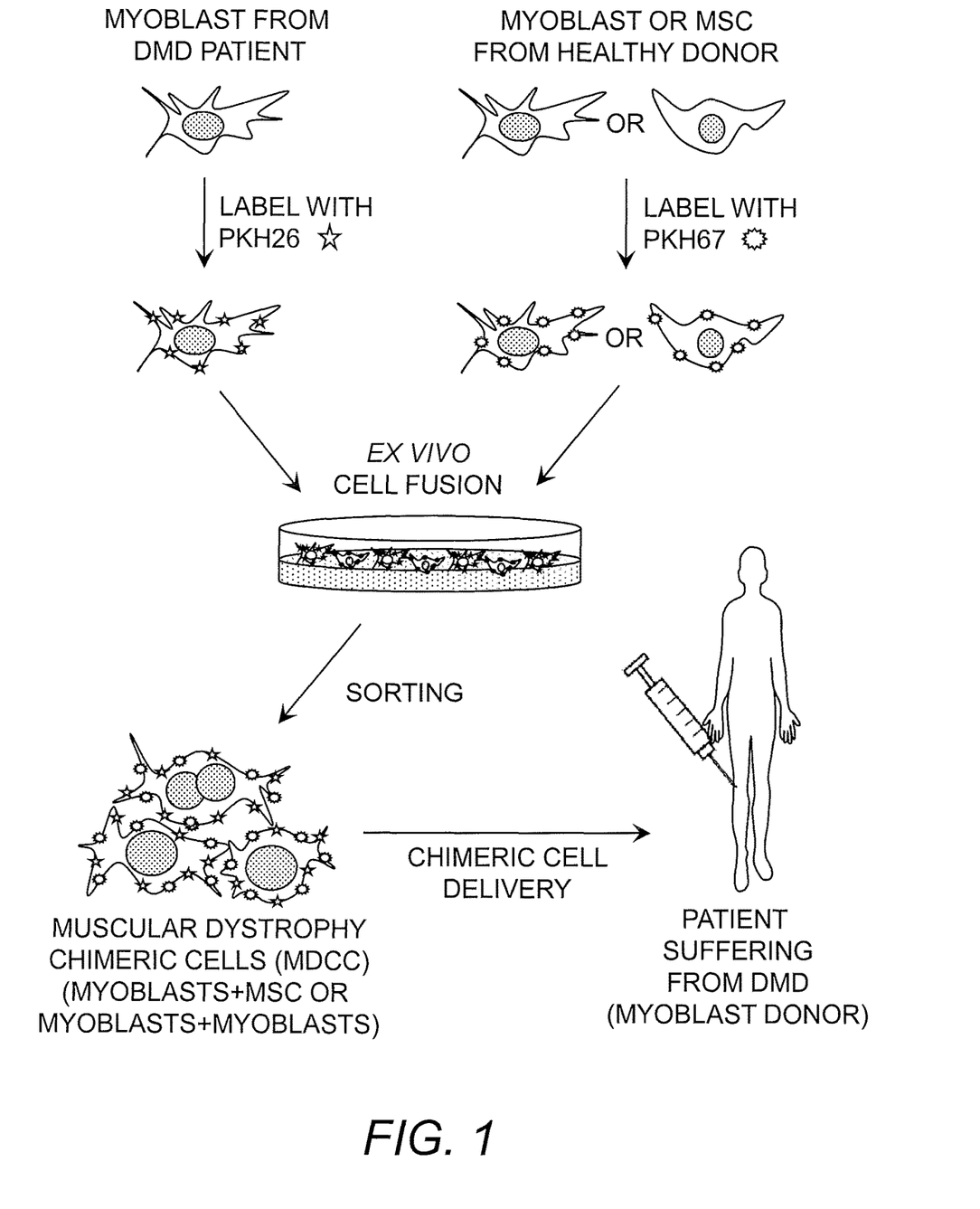
Figure 2:
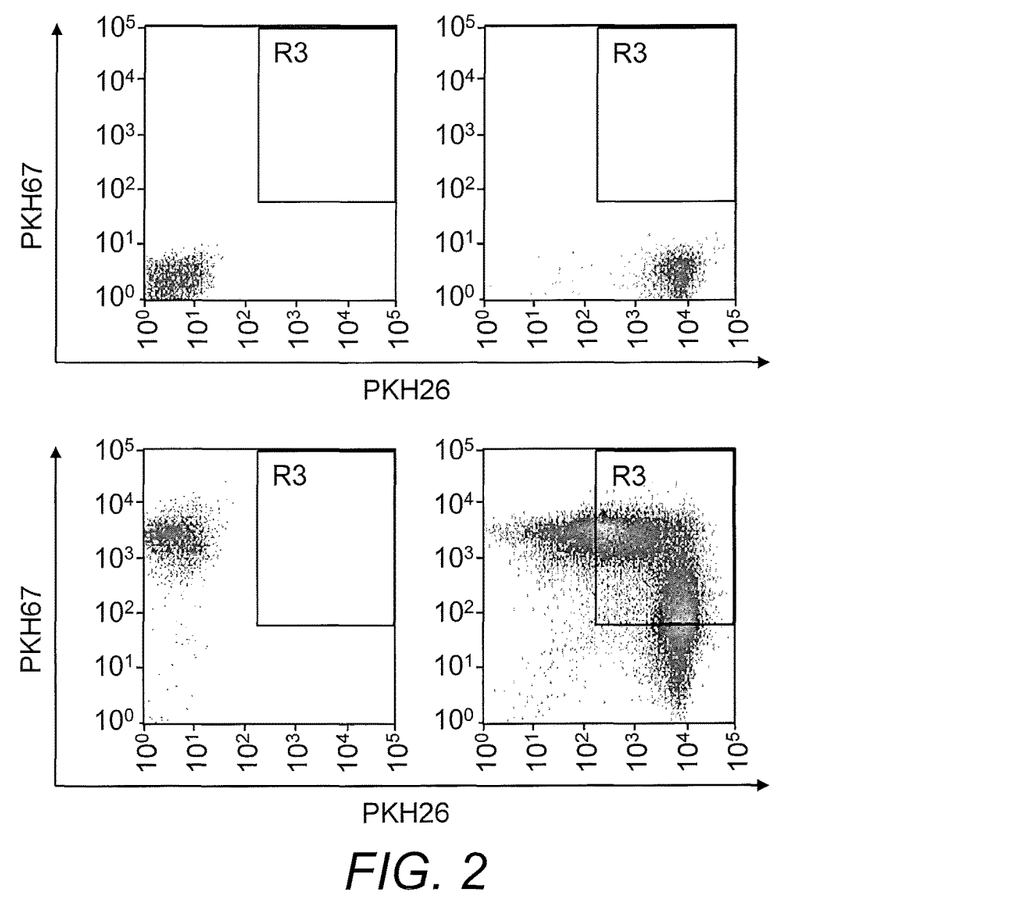
FIG. 2 shows flow cytometry analysis of ex vivo created (by fusion) human MD chimeric cells (hMDCC). Shown are dot plots of unstained myoblasts, PKH26-stained myoblasts, PKH67-stained mesenchymal stem cells (MSC), and fused PKH26/PKH67-stained cells, confirming creating of hMDCC.

Ex vivo fusions of allogenic human myoblasts and MSC or myoblasts from two unrelated donors were performed, using polyethylene glycol technique (FIG. 1). Briefly, commercially available (Lonza, Inc.) human myoblasts and MSC were separately cultured for 6 to 10 days. Next, cells were fluorescently labeled using either PKH-26 (red) or PKH-67 (green) tracking dye, as shown in FIG. 1. Fusion was performed using PEG. Cells presenting double (PKH26 and PKH67) staining were selected via fluorescently activated cell sorting (FACS; BD ASTERIOS). To confirm fusion, double (PKH26 and PKH67) labeled MDCC were evaluated using confocal microscopy and flow cytometry (FIG. 2). Morphology of MDCC was assessed using transmission electron microscopy. The MDCC were confirmed by the presence of two nuclei, fused cell membrane and fused cytoplasm.

Flow cytometry was used to assess phenotype changes of MDCC at 7, 14, 21 and 30 days following fusion. MDCC were tested for the expression of muscle-specific markers (Anti-Myogen in, Anti-hMyosin Heavy Chain, Anti-mMYF-5) and MSC markers (CD105, CD73, CD90). The results are shown in Table 2. Notably, the MDCC did not express CD45 or CD8 markers, which are characteristic for hematopoietic cells.

TABLE 2

| Phenotype | Sample | | |
| --- | --- | --- | --- |
| | Myoblast Donor A | Myoblast Donor B | MDCC after Fusion A + B |
| Anti-myogenin | + | − | + |
| Anti-hMyosin Heavy Chain | + | − | + |
| Anti-mMYF-5 | + | − | + |
| CD105 | − | + | + |

TABLE 2-continued

| Phenotype | Myoblast Donor A | Myoblast Donor B | MDCC after Fusion A + B |
|---|---|---|---|
| CD73 | − | + | + |
| CD90 | − | + | + |

Additionally, MDCC were analyzed by FISH to detect sex chromosomes and viability staining (Trypan blue). Further, MDCC were cultured for 30 days to test proliferation and secretory properties via ELISA assay. Moreover, using immunofluorescence staining, the expression of dystrophin was demonstrated in the human MDCC. In addition, in vitro results confirmed myogenic differentiation potential of hMDCC. After fusion, hMDCC were placed in specific myogenic differentiation medium (low serum medium supplemented with insulin, PROMOCELL) for 7 days. Skeletal myosin heavy chain expression, a marker of skeletal myocyte differentiation, was observed in all hMDCC lines.

To asses genotype and confirm cell fusion, Polymerize Chain Reaction-Reverse Sequence-Specific Probe (PCR-rSSOP) and short-tandem repeat-PCR (STR-PCR) was performed on MDCC, detecting HLA class I and II and specific gene combination from both donors (Tables 3 and 4, respectively). This analysis indicated that MDCC presented HLA alleles derived from both donor cells and showed the presence of genetic markers specific for both fusion donor cells.

TABLE 3

| HLA Type | Myoblast Donor A | Myoblast Donor B | MDCC after Fusion (A + B) |
|---|---|---|---|
| A | 01, 31 | 30, 30 | 01, 31, 30 |
| B | 08, 39 | 42, 57 | 08, 39, 42, 57 |
| Cw | 07, 07 | 17, 18 | 07, 07, 17, 18 |
| Bw | 6 | 6, 4 | 6, 4 |
| DRB1 | 03(17), 14 | 08, 03(18) | 03(17), 14, 08, 03(18) |
| DQB1 | 02, 03(7) | 03(7), 04 | 02, 03(7), 03(7), 04 |
| DR52, DR53 | 52 | 52 | 52 |

TABLE 4

| Genetic Marker | Myoblast Donor A | Myoblast Donor B | MDCC after Fusion (A + B) |
|---|---|---|---|
| D5S818 | 11, 12 | 11, 12 | 11, 12 |
| D7S820 | 8, 10 | 10 | 8, 10 |
| Th01 | 8, 9, 3 | 6, 7 | 8, 9, 3, 6, 7 |
| AMEL | X, Y | X | X, Y |
| TPOX | 9, 11 | 8, 9 | 9, 11, 8 |
| CSF1PO | 11 | 12 | 11, 12 |
| D21S11 | 28, 30 | 30, 31 | 28, 30, 31 |

In vitro culturing results showed proliferative potential, long-term viability and differentiation of DMDCC to the myocyte lineage. The expression of dystrophin was maintained by DMDCC up to 30 days post-fusion. Secretion of cytokines by DMDCC was confirmed by ELISA assay.

In in vivo studies, engraftment of locally administered hMDCC in mdx/scid mouse model was assessed. Five groups of mice were tested (Table 5). The first two groups included MDCC of myoblast/myoblast or MSC/myoblast origin (dose $0.5 \times 10^6$) delivered through multiple intramuscular injections following a standardized template, to the left gastrocnemius muscle of mdx/scid mice. Control groups included treatment with vehicle, treatment with unfused myoblasts (dose $0.5 \times 10^6$), or treatment with mixed MSCs and myoblasts (dose $0.5 \times 10^6$) via intramuscular injection. Outcomes measured included in vivo muscle function, dystrophin expression in treated muscles as well as MDCC engraftment at 1 week and 12 week time-points.

Dystrophin expression was used as a specific marker for hMDCC since it had been confirmed that both hMDCC lines expressed dystrophin. After 7 days following local intramuscular delivery of hMDCC, successful engraftment of hMDCC was shown. In addition, locally increased dystrophin expression (12%) was observed as early as 7 day post-transplant as compared with the lack of dystrophin expression in mdx/scid controls. Furthermore, at 90 days 17% of dystropin expression was observed.

TABLE 5

| Treatment | Time-point (days) | No. of Animals | Outcomes |
|---|---|---|---|
| Myoblast/MSC MDCC | 7 | 3 | MDCC engraftment and dystrophin expression (DE) |
|  | 90 | 3 | Muscle function and structure, DE |
| Myoblast/Myoblast MDCC | 7 | 3 | MDCC engraftment and DE |
|  | 90 | 3 | Muscle function and structure, DE |
| Myoblasts without fusion | 7 | 3 | MDCC engraftment and DE |
|  | 90 | 3 | Muscle function and structure, DE |
| Myoblast and MSC without fusion | 7 | 3 | MDCC engraftment and DE |
|  | 90 | 3 | Muscle function and structure, DE |
| Vehicle | 7 | 3 | MDCC engraftment and DE |
|  | 90 | 3 | Muscle function and structure, DE |

Another set of experimental groups (vehicle and hMDCC treated mdx/scid and wild type snj mice, n=3) were tested in motor function tests, including grip strength measurements and a wire hanging test. Ninety days after hMDCC therapy delivery, mice receiving hMDCC showed improvement (p=0.037) of grip strength and tolerance to fatigue on wire (mdx/scid mice, 50 gF; hMDCC therapy, 85-90 gF). Functional improvement was observed in groups treated with both MDCC lines when compared to vehicle treated groups until day 42. After this time-point only myoblast/myoblast hMDCC maintained increased muscle strength throughout the 90 day follow-up period. By comparison, grip strength values returned to baseline levels after 42 days in mice treated with MSC/myoblast hMDCC. The unfused cell treatment control groups showed temporary motor function improvement in the first 21 days only.

Figure 3A:
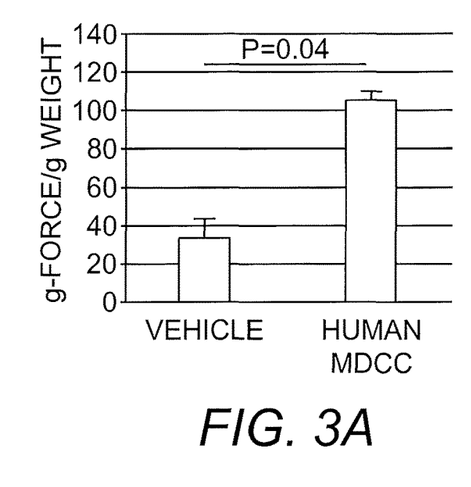
Figure 3B:
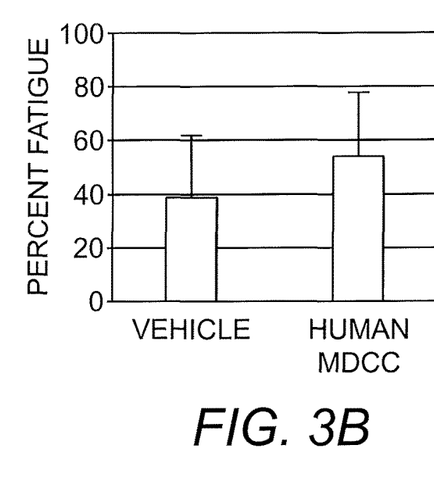

Gastrocnemius muscles harvested at 90 days after hMDCC delivery were analyzed in an ex vivo contractility test to assess muscle strength evoked by electric stimulation. Results showed that myoblast/myoblast hMDCC treated (FIG. 3A) muscle had significantly stronger contraction (p=0.04) even under induced strain (FIG. 3B). The same muscle samples were analyzed by confocal microscopy to detect and quantify dystrophin expression at 90 days after hMDCC treatment. On average, 17% of the cells were positive for dystrophin expression.

Currently, there is no effective therapy to treat DMD, a lethal genetic, neuromuscular disorder affecting 1 in every 3500 newborn boys. Treatment modalities, such as growth-modulating agents, anti-inflammatory or second-messenger signal-modulating agents, and molecular devices designed to skip mutations in the dystrophin gene have been attempted, however these approaches fail to halt or reverse disease progression. By comparison, the instant MDCC therapy represents a universal regenerative medicine approach for local or systemic application in patients suffering from DMD. Further, compared to other cell-based therapies, the unique features of MDCC, created through ex vivo fusion, are the combination and synergistic effects of the complementing characteristics of cells of myogenic and mesenchymal origin, such as high proliferation rate, capability for myogenic conversion, and secretion of immunomodulatory cytokines and growth factors facilitating muscle regeneration. Moreover, the preparation of MDCC does not require genetic manipulations or introduction of viral vectors to the cells, thus making it a safer therapy. In addition, since MDCC therapy is not gene/mutation-specific, it can be tailored and applied to patients suffering from other types of muscular dystrophies including, e.g., Becker dystrophy.

Example 2: Ex Vivo Preparation of Mouse Duchene Muscular Dystrophy Chimeric Cells (mDMDCC)

Healthy snj and mdx (dystrophin-deficient) primary myoblast cultures as well as mdx MSC cultures were established and expanded in vitro. Three murine myoblast/MSC and myoblast/myoblast fusions were performed with polyethylene-glycol technique. Dystrophin expression, as well as myogenic differentiation capacity, was confirmed before and after fusion.

In in vivo studies (Table 6), efficacy of murine DMDCC engraftment, survival and restoration of dystrophin expression and motor functions were tested 30 days following local delivery of mDMDCC to the gastrocnemius muscle. Of the five groups tested, mDMDCC composed of myoblast/myoblast and MSC/myoblast origin (dose $0.5 \times 10^6$) were delivered through multiple intramuscular injections following a standardized template, to the left gastrocnemius muscle of mdx mice. Control groups included treatment with vehicle, treatment with not unfused myoblast and treatment with mixed MSC and myoblast. Outcome measurements included in vivo muscle function, dystrophin expression in treated muscles as well as mDMDCC engraftment, which were assessed after 4 weeks. After myoblast/myoblast mDMDCC delivery, dystrophin expressing cells constituted 37% of total nucleated cells on immunofluorescence analysis by confocal microscope. Myoblast/myoblast mDMDCC-treated muscle showed dystrophin-positive and dystrophin-negative areas. Dystrophin-positive cells were characterized by dystrophin expression on the membrane (normal pattern) as well as cytoplasmic expression.

TABLE 6

| Treatment | Time-point (days) | No. of Animals | Outcomes |
|---|---|---|---|
| Myoblast/MSC MDCC | 90 | 4 | Muscle function and structure, DE |
| Myoblast/Myoblast MDCC | 90 | 4 | MDCC engraftment, muscle function and structure, DE |

TABLE 6-continued

| Treatment | Time-point (days) | No. of Animals | Outcomes |
|---|---|---|---|
| Myoblasts without fusion | 90 | 4 | MDCC engraftment, muscle function and structure, DE |
| Myoblast and MSC without fusion | 90 | 4 | MDCC engraftment, muscle function and structure, DE |
| Vehicle | 90 | 4 | MDCC engraftment, muscle function and structure, DE |

Figure 4A:
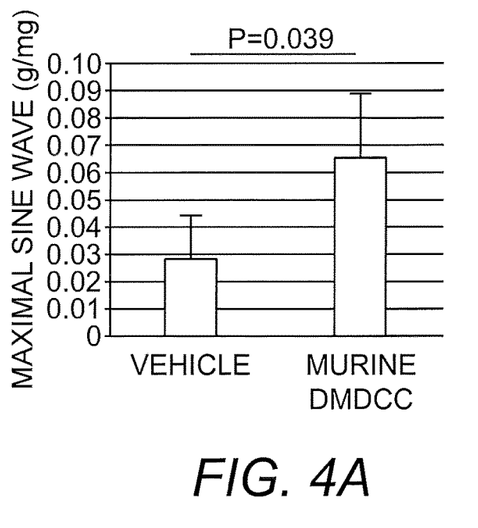
Figure 4B:
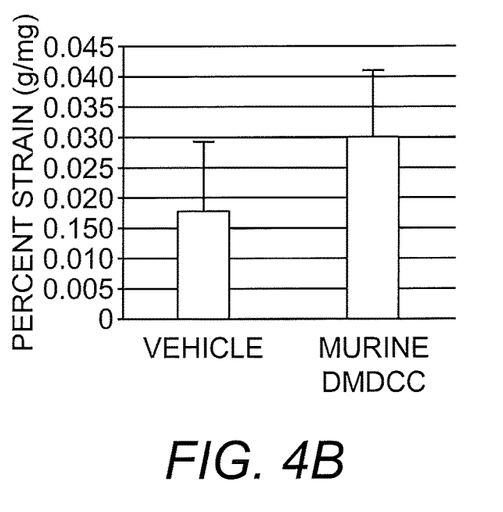
Figure 5A:
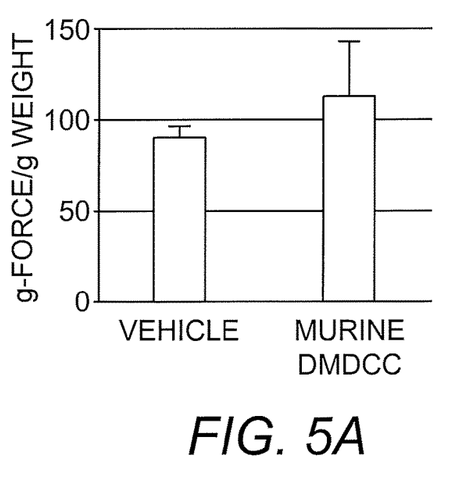
Figure 5B:
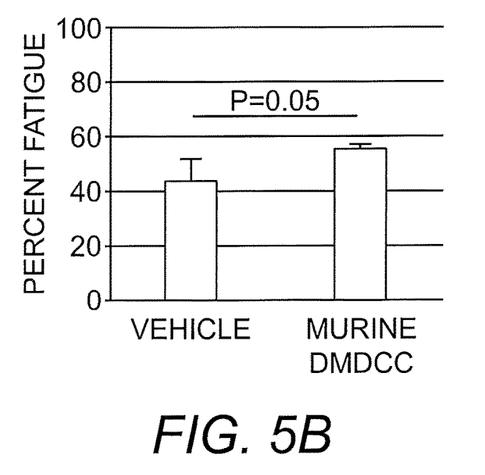

Interestingly, mDMDCC-treated muscles showed decreased muscle weight as compared to contralateral untreated muscles. The lower weight of the treated muscle can be explained by decreased DMD-related hypertrophy and fibrosis. Despite the reduced muscle weight, muscle force measurements, evoked with electric stimulation in situ, resulted in increased values of muscle strength in vivo (FIGS. 4A and 4B) as well as ex vivo (FIGS. 5A and 5B).

In vivo motor function evaluated by grip strength and wire hanging tests also confirmed the efficacy of mDMDCC with increased grip strength and prolonged time to resist fatigue. Myoblast/Myoblast mDMDCC-treated muscle maintained higher strength values than muscles treated with myoblast/MSC MDCC, which did not differ from control muscle values 30 days after therapy delivery. Myoblast-derived mDMDCC treatment resulted in increased tolerance for fatigue, shown by longer hanging time on wire compared to control animals.

What is claimed is:

1. An isolated Muscular Dystrophy Chimeric Cell (MDCC) population comprising cells produced by ex vivo fusion and expansion of
   (a) a first myoblast; and
   (b) a second myoblast, mesenchymal stem cell, or stromal cell,
   wherein at least one of the first myoblast, second myoblast, mesenchymal stem cell, or stromal cell is from a healthy donor and the other is a dystrophin deficient cell from a subject suffering from a muscular dystrophy, and
   wherein the mesenchymal stem cell and stromal cell are not genetically modified, and the first myoblast and second myoblast are from different donors.

2. The isolated MDCC of claim 1, wherein the first myoblast, second myoblast, mesenchymal stem cell, or stromal cell is autologous or allogeneic.

3. The isolated MDCC of claim 1, wherein the healthy donor is the subject's father.

4. The isolated MDCC of claim 1, wherein the mesenchymal stem cells are derived from bone marrow or adipose tissue.

5. The isolated MDCC of claim 1, wherein said MDCC secretes one or more immunomodulatory cytokines and growth factors.

6. The isolated MDCC of claim 5, wherein the one or more immunomodulatory cytokines and growth factors comprise insulin-like growth factor 1, hepatocyte growth factor and myostatin.

7. The isolated MDCC of claim 1, wherein said ex vivo fusion is between: a) a dystrophin deficient human myoblast from a subject suffering from a muscular dystrophy and a human myoblast from a healthy donor; b) a dystrophin deficient human myoblast from a subject suffering from a muscular dystrophy and a human mesenchymal stem cell from a healthy donor; or c) a human myoblast from a healthy donor and a dystrophin deficient human mesenchymal stem cell from a subject suffering from a muscular dystrophy; or d) a dystrophin deficient human myoblast from a subject suffering from a muscular dystrophy and a human stromal cell from a healthy donor.

8. A composition comprising the isolated MDCC of claim 1 and a pharmaceutically acceptable carrier.

9. A method of treating a muscular dystrophy comprising administering to the subject in need of treatment an effective amount of the isolated MDCC of claim 1 thereby treating the subject's muscular dystrophy.

10. The method of claim 9, wherein the muscular dystrophy is Duchenne Muscular Dystrophy.

11. The method of claim 9, wherein said MDCC is administered by intravenous injection, intra-bone injection or intramuscular injection.

12. The MDCC of claim 1, wherein the ex vivo fusion is induced by polyethylene glycol.

* * * * *